United States Patent

Nyboer

[11] 4,008,712
[45] Feb. 22, 1977

[54] METHOD FOR MONITORING BODY CHARACTERISTICS

[75] Inventor: Jan Nyboer, Grosse Pointe, Mich.

[73] Assignee: J. M. Richards Laboratories, Grosse Pointe Park, Mich.

[22] Filed: Nov. 14, 1975

[21] Appl. No.: 632,038

[52] U.S. Cl. .................. 128/2.1 Z; 128/2.05 V
[51] Int. Cl.² ........................ A61B 5/05
[58] Field of Search ......... 128/2.1 Z, 2.1 R, 2.05 V

[56] References Cited

UNITED STATES PATENTS

| | | | |
|---|---|---|---|
| 2,184,511 | 12/1939 | Bagno et al. | 128/2.1 Z |
| 3,452,743 | 7/1969 | Reike | 128/2.1 Z |
| 3,730,171 | 5/1973 | Namon | 128/2.1 Z |
| 3,742,936 | 7/1973 | Blanie | 128/2.1 Z |
| 3,851,641 | 12/1974 | Toole | 128/2.05 V |
| 3,871,359 | 3/1975 | Pacela | 128/2.1 Z |

OTHER PUBLICATIONS

Mullick et al., "Diagnosis of Deep Electrical Impedance", The Am. J. of Surgery, vol. 119, pp. 417–422, Apr. 1970.

Geddes et al., "The Measurement...by Electrical Impedance, Am. J. of Med. Elec., Apr.–June, 1964, pp. 16–27.

Primary Examiner—Robert W. Michell
Assistant Examiner—Lee S. Cohen
Attorney, Agent, or Firm—Harness, Dickey & Pierce

[57] ABSTRACT

A method and apparatus for performing electrical measurement of body mutual electrical impedances to determine changes in total body water in normal and deranged states of the body. The apparatus is particularly useful in determining the progression of dialysis cases during the period when renal dialysis is being performed on the patient. The method and apparatus utilizes a special electrical circuit for measuring electrical characteristics at selected body locations. Certain electrical characteristics are measured such as the resistance, the capacitive impedance, and the total reactance of the body, and the phase angle is calculated or measured. Utilizing some of these measurements, the total body water relative to the body weight may be determined.

13 Claims, 3 Drawing Figures

METHOD FOR MONITORING BODY CHARACTERISTICS

BACKGROUND AND SUMMARY OF THE DISCLOSURE

This invention relates generally to a system for measuring physical characteristics of the body by a non-invasive and atraumatic process and apparatus and, more specially, to a method and apparatus for measuring water in the body by measuring certain electrical characteristics of the body by means of a four-electrode bridge or phase sensitive potentiometer technique.

In renal dialysis of a patient, it is important to know the effects that the dialysis procedure is having on the patient and to know the ultimate result of the dialysis procedure upon completion of the procedure. In view of the variations of weight from one patient to another, in order to properly evaluate the progression of the dialysis and the ultimate result of the dialysis, the starting weight and final weight of the patient must be known. Accordingly, in order to obtain these figures for comparison, it has been necessary to weigh the patient to determine a starting weight, a progression of loss of body weight, and an ultimate body weight after the completion of the dialysis. Thus, constant body weights must be taken before, during and after the dialysis to ascertain the benefits of the dialysis and a continuous control of weight loss is recommended. However, it has been found that the percentage of weight loss to total body weight during the renal dialysis procedure is an extremely small figure. Accordingly, this is not an accurate method of determining the benefits of the dialysis.

Further, prior procedures have included chemical tests which have been performed to determined specific blood chemistry or enzyme activity. This procedure requires blood samples to be taken from the patient, even though some patients are already suffering from an anemia condition. Also, this has not been found to be a satisfactory solution in view of the fact that there is not a continuous monitoring of the chemistry or enzyme activity nor are the results of sufficient accuracy to determine the benefits of the renal dialysis procedure.

The system of the present invention proposes an all electrical approach to the quantitative evaluation of the loss of body water relative to the total body weight to evaluate the reduction of body water or the planned stability of weight during the dialysis procedure. With the proposed system of the present invention, the physician may measure, with accuracy, the loss in body water or the lack of loss of water in the situation where certain molecules are being removed (as in the toxic patient) by measurement of certain impedance characteristics of the body by means of a intermediate radio frequency electrical signal which may be used to continuously monitor the patient. The method of the present invention is quantitative in the results provided and is non-invasive to the patient in that samples of body fluids are not removed from the patient for analysis. Further, it has been found that the percentage change in certain of the electrical characteristics measured by the system of the present invention provide a greater percentage change per unit of body water lost than heretofore known methods of determining body water loss.

Accordingly, it is one object of the present invention to provide an improved system for measuring the loss of body water or the control of body mass.

It is another object of the present invention to provide an improved system for measuring the loss of body fluid by use of electrical apparatus for measuring the mutual impedance of portions of the body of a patient.

It is another object of the present invention to provide an improved system for measuring the loss of body fluid of a portion or the entirety of the human body by comparing an electrical characteristic of the body taken before the water loss to the same electrical characteristic taken after the water loss.

It is still another object of the present invention to provide an improved electrical characteristic measuring system for determining the effectiveness of renal dialysis which measures the electrical characteristics having the greatest percentage change per loss of body water.

It is still another object of the present invention to provide an improved system for electrically measuring characteristics of the body indicative of the loss of body water during renal dialysis and particularly which measure the capacitive reactance and impedance angle of the body.

It is still another object of the present invention to provide an improved electrical system for measuring characteristics of the body representative of body water loss during renal dialysis which includes a four-electrode system for providing inputs to a vector voltmeter type of measuring instrument.

It is still a further object of the present invention to provide an improved system for measuring bio-electrical impedance during renal dialysis.

It is still another object of the present invention to provide an improved system for measuring the effects of renal dialysis which is continuous, quantitative and non-invasive.

It is still a further object of the present invention to provide an improved system for measuring the effects of renal dialysis which is simple to use and reliable in operation.

Further objects, features and advantages of the present invention will become readily apparent upon a reading of the following description and a study of the attached drawings in which.

DETAILED DESCRIPTION OF THE INVENTION AND THE DRAWINGS

Figure 1:
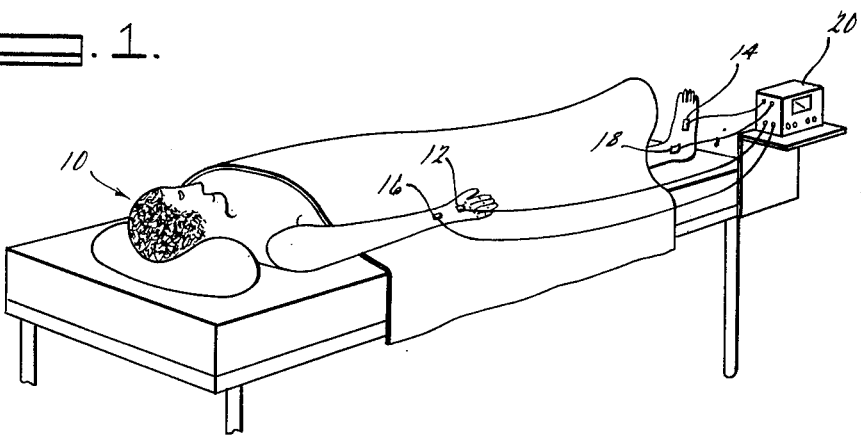
FIG. 1 is a view of a patient undergoing renal dialysis with the electrodes and a vector voltmeter attached to the patient in accordance with the principles of the present invention.

Referring now to FIG. 1, there is illustrated a patient 10 in the recumbent position with the arms parallel to the torso. The patient may either be prepared to undergo dialysis, in the process of undergoing dialysis, or have completed the dialysis procedure. In order to determine the electrical characteristics of the patient, constant current supply electrodes, held in place by Velcro straps or other fastening means, are positioned on the patient, one electrode 12 on the metacarpal-phalangeal region and a second electrode 14 is placed over the metatarsal-phalangeal region. The voltage or impedance detection (the current being constant) is made from two other electrodes 16, 18 placed across the wrist and ankle. Both pairs of electrodes are usually located on the side opposite to the arterial-venous fistula in use for dialysis. As is typical, the electrodes are wetted by conductive paste in order to enhance the current and voltage sensing characteristics of the electrodes at the skin.

In performing the measurements, the system utilizes a relatively high frequency source of electrical energy, for example 50 kilohertz at a constant current, and a vector voltmeter 20 is used having a capability of reading the resistance of the body in ohms, the capacitive reactance in ohms, and the total impedance in ohms and preferrably phase angle in degrees. The constant current source is fed to the two electrodes 12, 14 to cause a current to flow in the body between the two electrodes 12, 14. This creates a voltage drop between the electrodes 12, 14 and a portion of that drop is picked off by means of electrodes 16, 18. In view of the fact that the current supplied by electrodes 12, 14 is constant, the impedance between electrodes 16, 18 is directly proportional to the voltage.

In making the electrical measurements described above, the resistance, capacitive reactance, total impedance and phase angle, it has been found that a phase sensitive voltmeter is preferably utilized at frequencies in a range from a low frequency alternating current to current in the intermediate frequency range. Under certain circumstances, a direct current source may be used to obtain information on the optimum conductance related to extracellular pathways only, to be explained hereinafter. Experiments have been performed in the 50 kilohertz range and it is believed that the best results for measuring total body water occur between 5 megahertz and 50 megahertz. It is to be noted that the switching of a direct current source from off to on, or vice versa, creates a high frequency current flow at the transition point and before the steady state of the current, the frequency depending on the impedance of the circuit. In calculating the total body water at 50 kilohertz, the following formula is presently used:

Liters Body Water = $0.4362 \, T^2/R + 12.3374$ in which T is the height of the patient in centimeters and R is the resistive impedance to the high frequency current of 0.80 milliampere. Subsequently, the angle $\theta$ is calculated from the resistance and capacitive reactance measurements if the angle $\theta$ is not read directly.

In determining the frequency to be used, it is believed that the low frequencies, including direct current flows in the extracellular fluid and does not penetrate the cell walls of the blood cells and other cells within the whole blood. On the other hand, the higher frequencies do penetrate the cell walls and current flows through all of the matter in the whole blood including the inner portion of the cells. Thus, the low frequencies provide a measurement of the impedance characteristics of the extracellular fluid and the higher frequencies provide a measurement of the impedance characteristics of the total fluid mass. It is to be noted that the direct current and high frequencies eliminate or minimize the reactive impedance component of the total impedance, and the total impedance substantially equals the resistance.

One of the objectives of hemodialysis is to reduce the salt present in the blood and to change the permeability of the cell membranes. In the body, the reactive capacitance or space is largely determined by the cellular masses which are semipermeable to alternating current, particularly of intermediate radio frequency. The cells act as small Leyden Jars which change their permeability physiologically. The ionic content of the extracellular composite is mainly resistive. The ratio of reactance space to resistance space is called the Q-factor or the power factor. This is also trigonometrically expressed as the tangent of the electrical impedance angle $\theta$. The study of translocation of fluid and electrolyte during dialysis uses all these electrical properties to describe the tissue change. Thus, the changes in body water during dialysis may be calculated from the resistive component of impedance.

The impedance device must accurately discriminate resistance and capacitance values of the body. The base impedance and the impedance phase angle may then be accurately computed from these dependent properties. After the electrodes are applied the measurements are completed in less than one minute. The principle calculations of body water are outlined below on the basis of resistive impedance, or the vector impedance.

It has been found that a normal male or female has certain predictable capacitive reactance and phase angle which may be used as the desirable result in the dialysis procedure. Thus, a patient undergoing dialysis may be continuously monitored to determine the starting point, progress, and termination point of the dialysis procedure. In some cases, as explained above, loss of body water is not the desired result, but rather it is desired to control or maintain the body water while altering the chemistry of the blood. This procedure is also adapted to the system of the present invention.

Figure 2:
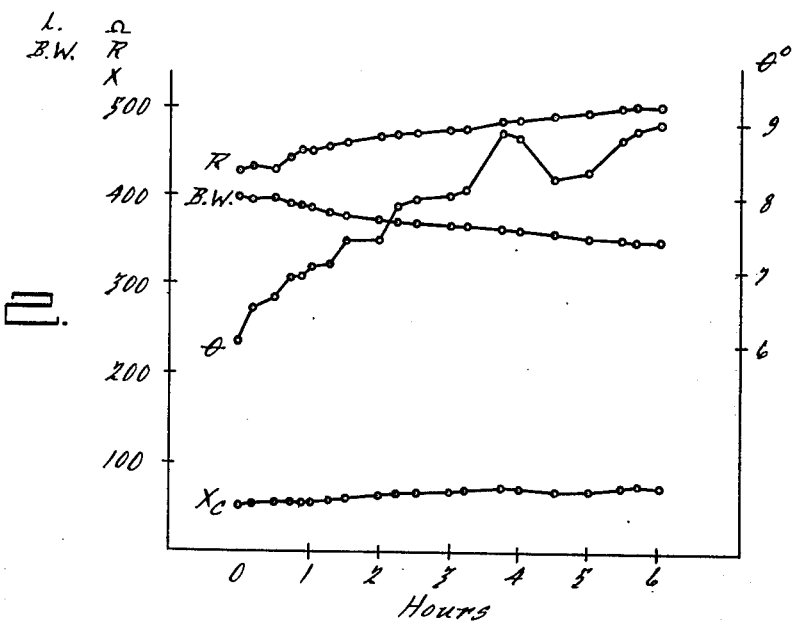
FIG. 2 is a plot of the reactive capacitance, the resistance, the phase angle and body weights as compared to dialysis time as taken in accordance with the procedure illustrated in FIG. 1.
Figure 3:
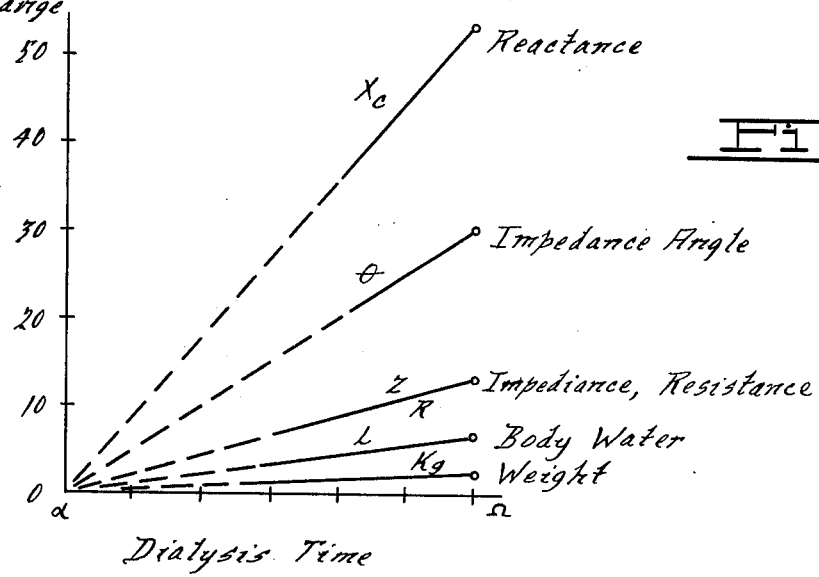
FIG. 3 is a plot of the average percentage change of the body weight, body water, impedance resistance, impedance angle and reactance as compared to dialysis time of a number of subjects.

Referring now to FIG. 2, there is seen a chart depicting the characteristics of a patient undergoing dialysis. It is seen that the body water decreases while the electrical characteristics of the patient increased. As is seen from FIG. 3, the most significant changes occurred in the case of the capacitive reactance and the phase angle as the dialysis is progressed. Specifically, the percentage change in reactance was in excess of fifty percent and the percentage change in the phase angle was in excess of thirty percent. The chart of FIG. 3 is illustrative of the percentage change for a number of patients tested while the chart of FIG. 2 was for a single patient. The phase angle change is approximately 4 hours occurred because the dialysis was discontinued and the patient ingested food.

In appendix A is illustrated a table giving data taken on a number of normal and abnormal patients. The mean numerical data developed by electrical impedance measurement in 51 normals and 28 abnormal cases of water metabolism are shown in Table 1. The abnormal cases are studied before and after dialysis as prescribed by the attending physicians. The normal cases had no history of renal, cardiac or proven endocrine imbalance.

Statistically significant differences in physical measurements of height, weight and surface area between the two sexes are present both in the control normal and the abnormal dialysis groups. The mean age of the normal female is 32, of the normal is 33, of abnormal female is 41 and of the abnormal male group is 38. Leaness and obesity do influence some of the electrical measures but it is of little concern in our present thesis of identifying electrical differences created by water gain or loss in the body compartments.

The calculated body water is significantly greater by about 10 liters in the normal male as compared to the normal female, i.e., 42 vs 32 L. The numerical values of TBW before dialysis in the abnormal groups are 2 to 3 percent higher than that present in the normal group. After dialysis of 4 to 6 hours the electrically identified water space decreases about 3.1 L. for the males and 2.6 L. for the females. The male group shows a larger TBW than the females before and after dialysis. Each sex group loses weight with dialysis. The males lose an average of 1.67 kg. while the females lose 1.43 kg. per subject.

The wrist to ankle electrical *resistance* and *impedance* is larger in the normal female than a male by about 140 ohms. The *resistance* in the female exceeds the male by 100 ohms in the abnormal group. See FIG. 4. On dialysis the males increase resistance by about 53 ohms while the females change by 81 ohms for about the same percent change of body water/weight. The maximum change in resistance or impedance during dialysis is about 150 ohms. This occurs in our most obese male subject. There is a decrease in resistance created by saline infusions.

The electrical *impedance phase angle* is significantly lower in the normal female, 5.1°, as compared to the normal adult male, 6.5°. The phase angles are lower than normal in both sexes during advanced renal impotence, i.e. 3.3° female and 5°.0 male. On hemodialysis the phase angles usually rise or approach the normal levels, i.e. 4.7° female and 6.7° male, unless this is counteracted by physiological saline infusions which balance or reverse this phenomenon.

The mutual impedance method offers a non-traumatic means of following body water quantitatively during the course of renal dialysis. Body water expressed in absolute terms or as a percent of body weight is significantly reduced by the dialysis. The body reactance between wrist and ankle, which had been significantly lower than normal prior to dialysis, is restored electrophysically back towards or beyond the average normal value by the procedure. This normalization of altered cell membrane function is additionally reflected in the electrical phase angle. Thus electrical impedance plethysmography uniquely provides many useful quantitative indices of water metabolism in patients with renal failure.

While the above discussion was couched in the framework of a comparison of the measured impedance characteristics to the established standard by human means, it is to be understood that the comparison may be made by several automatic methods, as for example by a preset electrical circuit which compares the input analog signal to a standard signal, whether the signals are digitized or not, or by programming a computer with a standard normalization curve and comparing the sensed input signals to the computer with the standard curve.

While it will be apparent that the preferred embodiment of the invention disclosed is well calculated to fulfill the objects above stated, it will be appreciated that the invention is susceptible to modification, variation and change without departing from the proper scope or fair meaning of the sub-joined claims.

| Variable | NORMAL | | | P-Value M vs. F (51) | ABNORMAL | | | | M + F (28) B→A |
|---|---|---|---|---|---|---|---|---|---|
| | Male (33) | Female (18) | M + F (51) ± S.D. | | Male (17) | | Female (11) | | |
| | | | | | Before(B) | After(A) | Before(B) | After(A) | |
| Height cm. | 176.4 | 162.6 | 171.5 ± 9.8 | <.0001 | 178.5 | — | 162. | — | 172.±11.3 |
| Weight kg. | 77.6 | 55.2 | 69.7 ± 16.2 | <.0001 | 77.07 | 75.30 | 55.61 | 54.18 | 68.6 →67.0 |
| Body Water L. | 41.98 | 31.85 | 38.41 ± 6.3 | <.0001 | 42.21 | 39.11 | 32.71 | 30.11 | 38.5–35.6 |
| % B.W./wt. | 55.2 | 58.2 | 56.3 ± 7.6 | N.S. | 56.40 | 53.63 | 59.98 | 56.82 | 57.8–54.9 |
| Resistance ohms | 461.4 | 601.3 | 510.8 ± 92 | <.0001 | 470.5 | 523.9 | 572.6 | 653.5 | 511.–575. |
| Reactance ohms | 52.31 | 52.48 | 52.37 ± 9.2 | N.S. | 41.09 | 60.96 | 33.38 | 53.54 | 38.1–58.0 |
| Impedance ohms | 464.5 | 603.7 | 513.6 ± 92 | <.0001 | 472.5 | 528.0 | 573.7 | 655.8 | 512–578 |
| Phase Angle, $\theta°$ | 6.486 | 5.059 | 5.983 ± 1.2 | <.0001 | 5.021 | 6.670 | 3.335 | 4.660 | 4.4–5.9 |

| Variable | P-Value M + F (28) B vs. A | NORMAL vs. ABNORMAL | | |
|---|---|---|---|---|
| | | P-Value All norm. (51) vs. All Pts. (28) Bef. Dial. | P-Value M norms. (33) vs. M Pts. (17) Bef. Dial. | P-Value F norms. (18) vs. F Pts. Bef. Dial. |
| Height cm. | | | | |
| Weight kg. | <.0001 | N.S. | N.S. | N.S. |
| Body Water L. | <.0001 | N.S. | N.S. | N.S. |
| % B.W./wt. | <.0001 | N.S. | N.S. | N.S. |
| Resistance ohms | <.0001 | N.S. | N.S. | N.S. |
| Reactance ohms | <.0001 | <.0001 | <.01 | <.001 |
| Impedance ohms | <.0001 | N.S. | N.S. | N.S. |
| Phase | | | | |

| | -continued | | | |
|---|---|---|---|---|
| Angle, θ° | <.0001 | <.0001 | <.01 | <.001 |

APPENDIX "A"

What is claimed is:

1. In a method of dialysis of a patient in which there is an established selected electrical characteristic having a normal magnitude indicative of a normal body fluid condition and which electrical characteristic changes in response to dialysis, the steps comprising: attaching a first pair of electrodes to the patient, attaching a second pair of electrodes to the patient, supplying an electrical signal to said first pair of electrodes, operating on said electrical signal via said second pair of electrodes to provide an indication of the measured magnitude of the selected electrical characteristic of the patient, performing dialysis on the patient, monitoring the change in magnitude of the selected electrical characteristic as a result of dialysis on the patient and comparing the change in magnitude of the selected electrical characteristic as measured on the patient with said normal magnitude whereby an indication of the effectiveness of the dialysis can be determined.

2. The method of claim 1 wherein said selected electrical characteristic is the electrical impedance of the patient between selected ones of said electrodes.

3. The method of claim 2 wherein said electrical characteristic includes resistance and capacitive reactance.

4. The method of claim 3 wherein said electrical signal is generated from a constant current source.

5. The method of claim 2 wherein said characteristic includes the transfer impedance of the electrode network.

6. The method of claim 5 wherein said transfer impedance is the ratio of the voltage between the second pair of electrodes to the current between the first pair of electrodes.

7. The method of claim 1 wherein said characteristic is the phase angle of the impedance of the patient between selected ones of said electrodes.

8. The method of claim 7 wherein said electrical signal is generated from a constant current source.

9. The method of claim 1 wherein said electrical signal is an alternating current signal of a preselected frequency and wherein said characteristic is the capacitive reactance of the patient between selected ones of said electrodes.

10. The method of claim 9 wherein said electrical signal is generated from a constant current source.

11. The method of claim 9 wherein said preselected frequency is less than 50 megahertz.

12. The method of claim 1 with said dialysis being terminated upon said measured magnitude attaining a preselected relationship to said normal magnitude.

13. The method of claim 12 with one of said first pair of electrodes being placed on the metacarpal-phalangeal region and the other placed over the metatarsal-phalangeal region and with said second pair of electrodes being located proximate the associated wrist and ankle of said regions.

* * * * *